United States Patent [19]

Burkinshaw et al.

[11] Patent Number: 4,996,383
[45] Date of Patent: Feb. 26, 1991

[54] INERT PURGE IN CATALYTIC DIMERIZATION OF OLEFINS

[75] Inventors: Jeffrey R. Burkinshaw, Bartlesville; Leo L. Gingerich, Nowata, both of Okla.

[73] Assignee: Phillips Petroleum Company, Bartlesville, Okla.

[21] Appl. No.: 503,599

[22] Filed: Mar. 26, 1990

[51] Int. Cl.$^5$ .............................................. C07C 2/04
[52] U.S. Cl. ................................. 585/516; 585/530; 585/531
[58] Field of Search ...................... 585/516, 530, 531

[56] References Cited

U.S. PATENT DOCUMENTS

| | | | |
|---|---|---|---|
| 3,253,047 | 5/1966 | Bellinger | 260/667 |
| 3,594,441 | 7/1971 | Grebbell et al. | 585/516 |
| 3,689,587 | 9/1972 | Grebbell et al. | 585/516 |
| 4,327,238 | 4/1982 | Eastman | 585/661 |
| 4,544,790 | 10/1985 | Drake | 585/516 |
| 4,609,637 | 9/1986 | Drake | 502/174 |

FOREIGN PATENT DOCUMENTS

| | | | |
|---|---|---|---|
| 755134 | 3/1967 | Canada | 585/516 |
| 978590 | 10/1962 | United Kingdom | 585/516 |

Primary Examiner—Asok Pal
Attorney, Agent, or Firm—Archie L. Robbins

[57] ABSTRACT

In processes for dimerization of olefins in the presence of potassium catalysts, plugging of the catalyst bed may be avoided by purging with certain aliphatic hydrocarbons.

12 Claims, 3 Drawing Sheets

INERT PURGE IN CATALYTIC DIMERIZATION OF OLEFINS

BACKGROUND OF THE INVENTION

This invention relates to a process for dimerization of olefins.

It is well known in the art to employ supported alkali metal catalysts for such conversions as propylene dimerization. It is also well known to use alkali metal carbonates as catalyst support. For example, the use of potassium on potassium carbonate for the catalytic dimerization of propylene to 4-methyl-1-pentene has been disclosed in U.S. Pat. No. 4,544,790, U.S. Pat. No. 4,609,637 and U.S. Pat. No. 4,656,154. Typically, in the process of propylene dimerization to 4-methyl-1-pentene, the propylene is passed over a catalyst bed comprising extruded potassium carbonate impregnated with potassium metal. However, when this process is started up or shut down more than twice, it is observed that the catalyst bed is plugged, presumably by polymeric products formed during startups and shutdowns even though on shutdown the temperature is lowered to a range where polymerization would not be expected. The plugged catalyst bed must therefore be replaced, incurring additional cost and time.

SUMMARY OF THE INVENTION

It is an object of this invention to provide a process for dimerization of olefins in the presence of a potassium catalyst so as to avoid clogging of the catalyst bed.

In accordance with this invention dimerization of a hydrocarbon is carried out in the presence of an alkali metal catalyst on a potassium carbonate substrate using the successive steps of:
(1) charging catalyst to the reactor;
(2) purging the reaction system with an inert fluid;
(3) contacting the dimerizable organic compound with the dimerization catalyst;
(4) porging the reaction system with an inert fluid.

BRIEF DESCRIPTION OF THE DRAWINGS

In the drawings which form a part thereof.

DETAILED DESCRIPTION OF THE INVENTION

Figure 1:
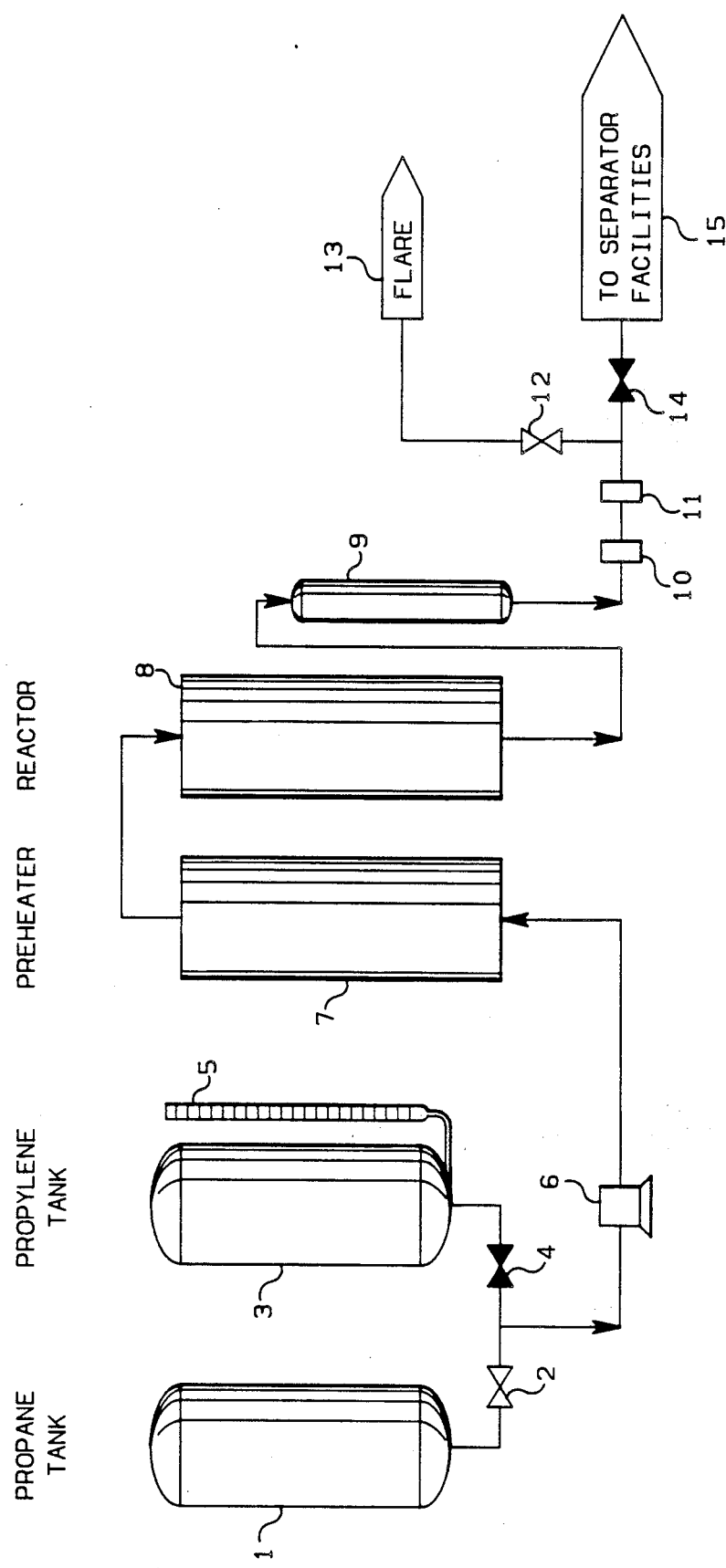
FIG. 1 is a schemetic of the process at time of startup using propane.

Reactants for which this process is contemplated as useful are olefinic compounds which can (a) self-react, i.e., dimerize, to give useful products such as, for example, the self-reaction of propylene gives 4-methyl-1-pentene; and/or (b) olefinic compounds which can react with other olefinic cmpounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those ocmpound designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylis hydrogen must, however, be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

The invention method is particularly appropriate in the conversion of propylene to 4-methyl-1-pentene.

Catalysts for which the purging process of this invention is contemplated as useful are those having a potassium carbonate support, at least one elemental alkali metal and optionally one or more of the following promoters: elemental copper, elemental cobalt, finely divided stainless steel, and mixtures of two or more thereof. It should be recognized, however, that the catalysts of the invention can contain additional components which do not adversely affect the catalyst performance, such as, for example, pigments, dyes, processing aids, inert fillers, binders and the like. Preferably the catalyste consist essentially of an extruded potassium carbonate support, potassium and one or more of the above-identified promotors.

The proportion of promoter combined with the potassium carbonate support can vary apprciably, but generally, when a promoter is used, at least one weight percent of that promoter based on the total weight of treated support will be employed.

This invention is contemplated to be useful when alkali metals such a lithium, sodium, potassium, rubidium and cesium are being used. While the proportion of alkali metal combined with the potessium carbonate support can vary appreciably, generally at least about one weight percent of alkali metal based on the total weight of treated support will be employed. Similarly, potassium is the preferred alkali metal due to its ready availability as well as ease and safety in handling.

The potassium carbonate support for the catalyst may be prepared by any of several suitable means, including a "wet process" by mixing with water to a paste, drying and fractionating; or in a "melt process" by mixing with a non-acidic inorganic oxide support, heating, then cooling for treatment with metals.

The dimerization catalyst presently preferred in the process of this invention is a composition comprising about 4 to 8 percent by weight potassium metal catalyst on about 92 to 96 percent by weight extruded potassium carbonate substrate.

Aliphatic $C_2$ to $C_5$ hydrocarbons such as ethane, propane, butane, isobutane and pentanes or mixtures of these hydrocarbons may be used as the inert purge fluid. These are inert fluids with respect to this dimerization process and result in alleviation of catalyst bed plugging problems. Presently preferred is propane.

It is believed that purging with the inert fluid prevents plugging of the catalyst bed by preventing stagnant dimerizable organic compounds from reacting on the catalyst bed to form polymers. However, applicants do not wish to be bound by theory.

The dimerization reaction of this invention can be carried out using either batch or continuous types of operation, although the invention is perhaps more particulary useful for continuous types of operation which have to be shut down and restarted from time to time.

The dimerization process of this ivention can be carried out by means of any apparatus whereby there is achieved contact of the catalyst with the dimerizable organic compound; suitable equipment such as, for example, autoclaves, tubular reactors and the like as well known in the art can be employed. No special materials of construction are required so that steel, stainless steel, glass-lined reactors, or the like can be employed. The process is in no way limited to the use of a particular apparatus. The process of this invention can be carried out using a fixed catalyst bed, fluidized catalyst bed or moveing catalyst bed. Presently the invention is considered most useful for dimerization with a fixed catalyst bed.

Referring now to FIG. 1, inert fluid from a first tank 1 is used to purge the reaction system after introduction of the catalyst while the reactor temperature, pressure and flow rate are brought to desired levels.

The initial inert fluid purge is made when the reactor is from ambient temperature to about 160° C. After passing through the valve 2, positive displacement pump 6, preheater 7, reactor 8, cooling reactor 9, catalysis fines filter 10, mass flow meter 11 and valve 12, the purge fluid is flared at 13, as shown in FIG. 1.

Alternatively, rather than being flared, the purge fluid can be recycled after fractionation to remove possible contaminants such as polymer oligomers or heavy hydrocarbons. The purge fluid may also be used as fuel.

Any suitable purge time can be utilized. A purge duration of about 10 minutes will generally be long enough to clear residual dimerizable organic compounds from the reaction system. When the reactor and catalyst bed are at an elevated temperature from a previous reaction then it is usually advantageous to allow the purge to continue until the reactor and catalyst bed cools to ambient temperature, possibly as long as two or more hours but generally about 30 minutes. Therefore a purge duration ranging from about 7 minutes to about two hours is useful. More preferable is a purge range from about 10 minutes to about 45 minutes. Presently preferred is about 10 minutes for start up in a cool reactor and 30 minutes for start up of a reactor at elevated temperature or for shutdown of a system with elevated temperature.

Any suitable flow rate of the purge fluid may be utilized. Presently preferred is a purge fluid flow rate in the range of about 2 WHSV to about 8 WHSV.

Figure 2:
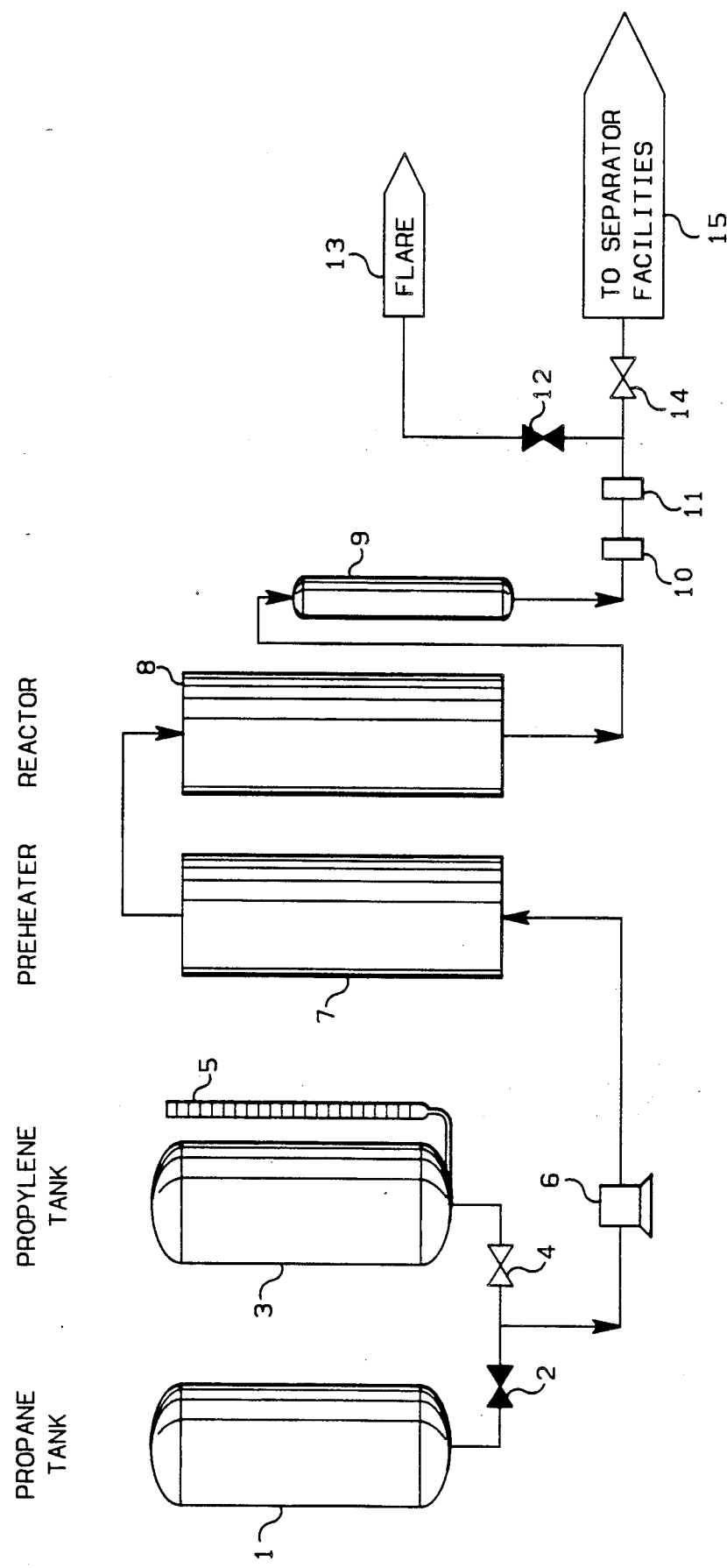
FIG. 2 is a schematic of the process after reaching desired temperature and pressure.

Following this startup procedure, a flow of the feedstock from a second tank 3 is substituted for the flow of the inert fluid from the first tank 1 by use of valves 2 and 4 and a positive displacement pump 6 as shown in FIG. 2.

The dimerizable organic compound is heated in a pre-heater 7 prior to contacting the catalyst with the dimerizable organic compound in the jacketed reactor 8. A cooling reactor 9 is typically followed by a catalyst fine filter 10 and a mass flow meter 11. The reaction product is then, by use of valves 12 and 14, directed to separator facilities 15.

Any suitable dimerization reaction time may be used in the dimerization process. The dimerization reaction time will generally be in the range of about 0.05 seconds to about 10 minutes and will preferably be in the range of about 0.1 second to about 5 minutes.

Any suitable catalytic dimerization temperature can be employed which provides the desired degree of catalytic activity in the dimerization of the organic feedstock. The dimerization temperature will generally be in the range of about 50° C. to about 250° C., more preferably be in the range of about 135° C. to about 170° C., and most preferably in the range of about 145° C. to about 165° C.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 1,000 to about 4,000 psig most preferred in order to achieve a good balance between reaction rate and minimizing equiment and operating costs necessitated by very high reaction pressures.

Any suitable feed rate for the organic feedstock can be utilized. The organic feedstock feed rate will generally be in the range of about 50 to about 5,000 volumes of gaseous feedstock per volume of catalyst per hour and will preferably be in the range of about 2 to about 8 kilograms of feedstock per kilogram of catalyst per hour.

Because the reaction is carried out in the liquid or supercritical phase, solvents or diluents for the reactants can be used. Saturated aliphatic hydrocarbons, e.g., pentane, hexane, cyclohexane, dodecane; and aromatic compounds, preferably those without an alpha-hydrogen (which would be capable of undergoing alkylation under the reaction conditions) such as benzene and chlorobenzene are suitable.

The contact time required for the dimerization reaction depends upon several factors such as, for example, the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours, although shorter and longer contact times can be employed. Preferably, times of about one minute to about 5 hours are employed.

Figure 3:
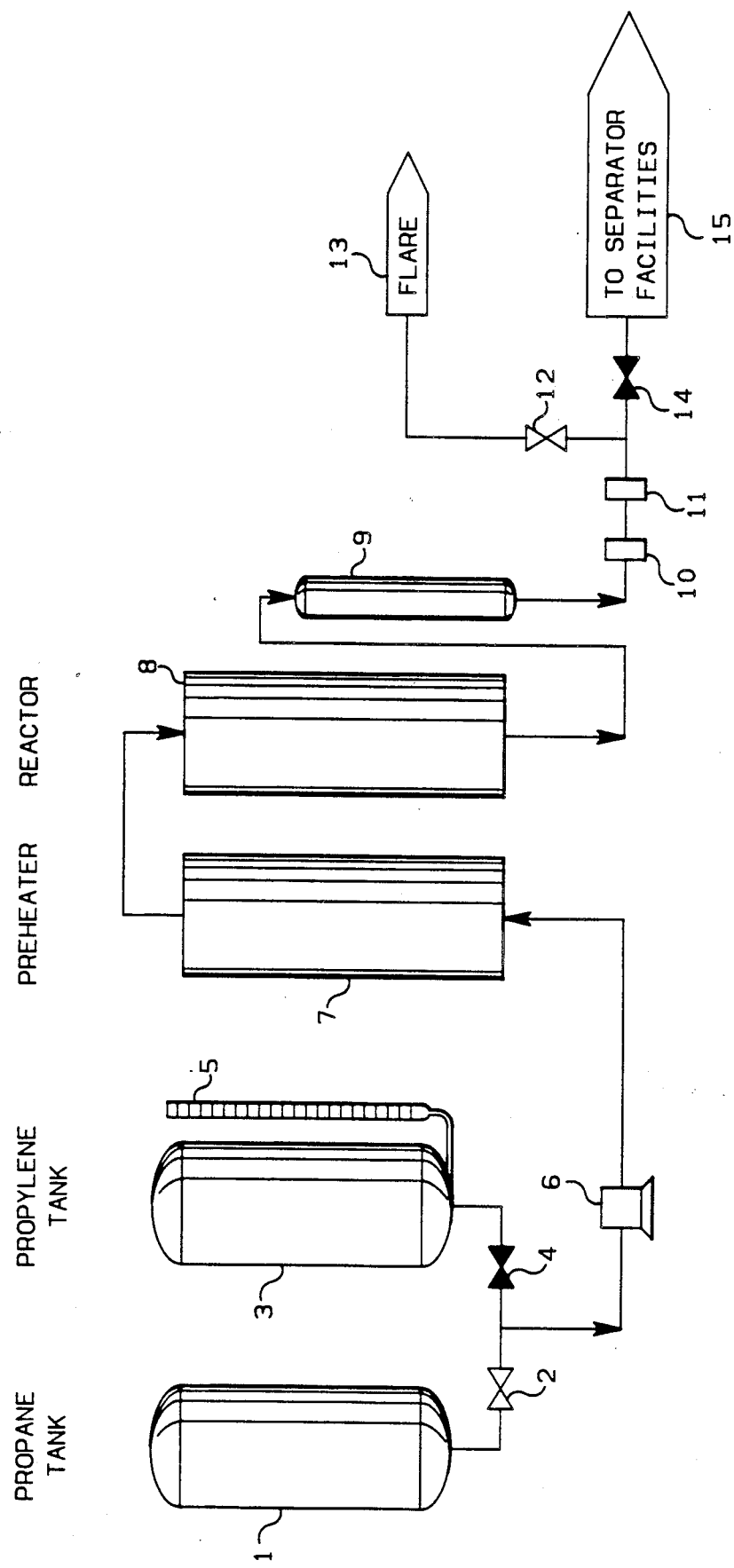
FIG. 3 is a schematic of the process after switch back to propane for shutdown of the reactor.

After dimerization is substantially complete, the flow of the organic feedstock is terminated and the reaction system is again purged with the inert fluid from tank 1 as shown in FIG. 3 for whatever is a suitable purge time, as discussed above. The temperature and pressure of the reactor 8 is returned to ambient levels.

The following examples are presented in further illustration of the invention.

EXAMPLE I

This example illustrates a typical continuous dimerization of propylene to 4-methyl-1-pentene (4MP1) without propane purging during startup and shutdown.

The experiment was carried out similar to FIG. 2 where liquid propylene in Tank 3 discharged with a flow of 3.0 weight hour space velocity and at a flow rate of 80 lbs/hr through a ball valve to a preheater 7. The reactionsystem was maintained at 1,400 psig to keep the propylene from being vaporized. The feed rate was controlled by a positive displacement pump 6 and was verified by a manual gage 5 that had bveen calibrated prior to startup and by a mass flow meter 11 at the end of the reaction or prior to discharging the reaction products to separation facilities 15.

The preheater 7 comprised a tube heat exchanger and was maintained at 145°C. by steam. The preheasted propylene was then discharged to and passed through a jacketed reactor 8 that was loaded with 27 lbs. of 4MP1 dimerization catalyst, 4% K on $K_2CO_3$, and was controlled isothermally by circulating a hot oil in the jacket. The reactor effluent comprising 4MP1, 4MP2, unreacted propylene and other byproducts was cooled to 49°C. (120°F.) and passed through an on-line filter 10 to a distillation column which is not within the scope of this invention.

The reactor was run continuously for 5 days during the week followed by shutdown at the end of the week. It was found that, after 2 startups and shutdowns, the catalyst bed was completely plugged because there was no feed flowing through the bed, as observed by the pressure drop from 1,400 psig to 0 psig. Although it was not analytically determined, the catalyst bed was presumably plugged up by polypropylene type polymer or oligomers.

EXAMPLE II

The experiment was similar to Example I except that, prior to each startup of the dimerization process and during each shutdown, the reaction system was purged with propane gas for 30 minutes to substantially remove any residual propylene remaining in the system to prevent it from being polymerized on the catalyst bed. Using this inventive process, it was found that the catalyst bed remained unplugged until it lost its catalytic activity after 60 to 70 days of operation with 2-day shutdowns for weekends.

That which is claimed is:
1. A method for catalytic dimerization using a dimerization catalyst comprising the steps of:
   (a) purging said dimerization catalyst during startup of said dimerization with an aliphatic hydrocarbon having 2 to 5 carbon atoms; and
   (b) thereafter substituting a dimerizable organic compound for said aliphatic hydrocarbon and flowing said dimeizable organic compound into contact with said dimerization catalyst.
2. A method in accordance with claim 1 comprising in addition:
   (c) during shutdown terminating said flowing of said dimerizable hydrocarbon and thereafter purging said dimerization catalyst with an aliphatic hydrocarbon having 2 to 5 carbon atoms.
3. A process according to claim 2 wherein:
   said catalyst comprises potassium metal on an extruded potassum carbonate substrate;
   and said dimerizable organic compound has from 3 to 30 carbon atoms per molecule and is characterized by having at least one olefinic double bond and at least one allylic hydrogen atom.
4. A method in accordance with claim 2 wherein said hydrocarbon is propane, said catalyst comprises potassium metal on an extruded potassium carbonate substrate, and said dimerizable organic compound is propylene.
5. A method in accordance with claim 4 wherein step (a) is about 30 minutes; wherein step (c) is about 30 minutes; and wherein said dimerizable organic compound is contacted with said dimerization catalyst on a fixed catalyst bed.
6. A method in accordance with claim 1 wherein said catalyst comprises potassium metal on an extruded potassium carbonate substrate, and said dimerizable organic compound is propylene.
7. A method in accordance with claim 1 wherein:
   said catalyst comprises potassium metal on a potassium carbonate support; and
   said dimerizable compound is at least one of:
   (a) an organic compound having from 3 to 30 carbon atoms per molecule, at least one olefinic double bond and at least one allylic hydrogen atom; and
   (b) an organic olefinic compound which does not have at least one allylic hydrogen atom but which is co-dimerizable.
8. A method for catalytic dimerization using a dimerization catalyst comprising the steps of:
   (a) contacting a dimerizable organic compound with said dimerization catalyst; and
   (b) thereafter terminating flow of said dimerizable organic compound and thereafter purging said dimerization catalyst with an aliphatic hydrocarbon having 2 to 5 carbon atoms.
9. A method in accordance with claim 8 wherein:
   said catalyst comprises potassium metal on an extruded potassium carbonate substrate;
   and said dimerizable organic compound has from 3 to 30 carbon atoms per molecule and is characterized by having at least one olefinic double bond and at least one allylic hydrogen atom.
10. A method in accordance with claim 8 wherein said hydrocarbon is propane, said catalyst comprises potassium metal on an extruded potassium carbonate substrate, and said dimerizable organic compound is propylene.
11. A method in accordance 10 wherein said step (b) is about 30 minutes; and wherein said dimerizable organic compound is contacted with said dimerization catalyst on a fixed catalyst bed.

12. A method in accordance with claim 8 wherein:
said catalyst comprises potassium metal on a potassium carbonate support; and
said dimerizable compound is at leat one of:
(a) an organic compound having from 3 to 30 carbon atoms per molecule, at least one olefinic double bond and at least one allylic hydrogen atom; and
(b) an organic olefinic compound which does not have at least one allylic hydrogen atom but which is co-dimerizable.

* * * * *

UNITED STATES PATENT AND TRADEMARK OFFICE
CERTIFICATE OF CORRECTION

PATENT NO. : 4,996,383

DATED : February 26, 1991

Page 1 of 2

INVENTOR(S) : Jeffrey R. Burkinshaw and Leo L. Gingerich

It is certified that error appears in the above-identified patent and that said Letters Patent is hereby corrected as shown below:

Column 1, line 40, the word "porging" should read "purging".

Column 1, line 44, the word "schemetic" should read "schematic".

Column 2, line 29, the word "ocmpound" should read "compounds".

Column 2, line 34, the word "allylis" should read "allylic".

Column 2, line 58, the word "catalyste" should read "catalysts".

Column 2, line 62, the word "apprciably" should read "appreciably".

Column 3, line 1, the word "potessium" should read "potassium".

Column 3, line 34, the word "ivention" should read "invention".

Column 3, line 45, the word "moveing" should read "moving".

Column 4, line 37, the temperature designation "$165^0C$" should read "$160^0C$".

Column 5, line 26, the word "reactionsystem" should read "reaction system".

Column 5, line 29, the word "gage" should read "gauge".

Column 5, line 29, the word "bveen" should read "been".

Column 5, line 34, the word "preheasted" should read "preheated".

UNITED STATES PATENT AND TRADEMARK OFFICE
CERTIFICATE OF CORRECTION

PATENT NO. : 4,996,383
DATED : February 26, 1991
INVENTOR(S) : Jeffrey R. Burkinshaw, et. al.

It is certified that error appears in the above-identified patent and that said Letters Patent is hereby corrected as shown below:

Column 6, line 6, the word "dimeizable" should read "dimerizable".

Signed and Sealed this

First Day of September, 1992

Attest:

DOUGLAS B. COMER

*Attesting Officer*  *Acting Commissioner of Patents and Trademarks*